United States Patent [19]
Masaki

[11] Patent Number: 4,960,125
[45] Date of Patent: Oct. 2, 1990

[54] DEVICE FOR LOW-FREQUENCY ELECTROTHERAPY IN A HUMID ENVIRONMENT

[75] Inventor: Kazumi Masaki, Osaka, Japan
[73] Assignee: Ken Hayashibara, Okayma, Japan
[21] Appl. No.: 265,291
[22] Filed: Oct. 26, 1988

Related U.S. Application Data

[63] Continuation of Ser. No. 89,954, Aug. 26, 1987, abandoned.

[30] Foreign Application Priority Data

Aug. 31, 1986 [JP] Japan .................................. 61-133326

[51] Int. Cl.$^5$ ............................................. A61N 1/32
[52] U.S. Cl. .................................. 128/421; 128/422; 338/12; 331/112; 331/113 R
[58] Field of Search ................... 338/12, 164; 335/207, 335/306; 128/421, 422; 331/112, 113 R; 323/369

[56] References Cited

U.S. PATENT DOCUMENTS

| | | | |
|---|---|---|---|
| 2,467,497 | 4/1949 | Ramos | 338/12 |
| 3,986,144 | 10/1976 | Russo | 331/113 R X |
| 4,249,537 | 2/1981 | Lee et al. | 128/422 |
| 4,372,319 | 2/1983 | Ichinomiya et al. | 128/422 |

Primary Examiner—Steven L. Stephan
Assistant Examiner—Emanuel T. Voeltz
Attorney, Agent, or Firm—Browdy and Neimark

[57] ABSTRACT

Disclosed is a novel device for low-frequency electrotherapy wherein a moisture proof variable resistor is used to control the output level of a low-frequency diphasic action potential circuit. The diphasic circuit produces a voltage having a pulse width of 0.1 to 10 seconds and a frequency off 10 to 300 Hertz superimposed on the voltage having a pulse interval of 0.1 to 10 seconds.

7 Claims, 4 Drawing Sheets

DEVICE FOR LOW-FREQUENCY ELECTROTHERAPY IN A HUMID ENVIRONMENT

This application is a continuation of application Ser. No. 089,954, filed Aug. 26, 1987, now abandoned.

BACKGROUND OF THE INVENTION

1. Field of the Invention

The present invention relates to a device for lowfrequency electrotherapy, specifically, directed to the use in a humid environment such as while having a bath.

2. Description of the Prior Art

One major problem in a conventional device is how to assure the moistureproofing and water-resistance of the power switch and variable resistor that is used as the output controller. Although an oscillator and a battery can be protected from moisture by enclosing them in a moistureproof container, protection of movable parts such as those in a variable resistor and a switch is very difficult.

SUMMARY OF THE INVENTION

The problem is overcome by providing a variable resistor comprising a resistive element, a sliding member slidable along with said resistive element, a moistureproof container enclosing said resistive element and sliding member, and a guide member, attached outside said container, movable magnetically in association with said sliding member; and controlling the output level by moving said sliding member.

More particularly, the present invention relates to a device for low-frequency electrotherapy wherein a variable resistor is used to control the output level, characterized in that said variable resistor comprises a resistive element, a sliding member slidable along with said resistive element, a moistureproof container enclosing said resistive element and sliding member, and a guide member, attached outside said container, movable magnetically in association with said sliding member; and that the output level is controlled by moving said sliding member.

BRIEF DESCRIPTION OF THE DRAWINGS

The present invention will hereinafter be explained with reference to the accompanying drawings, in which.

DESCRIPTION OF THE PREFERRED EMBODIMENTS

Figure 1:
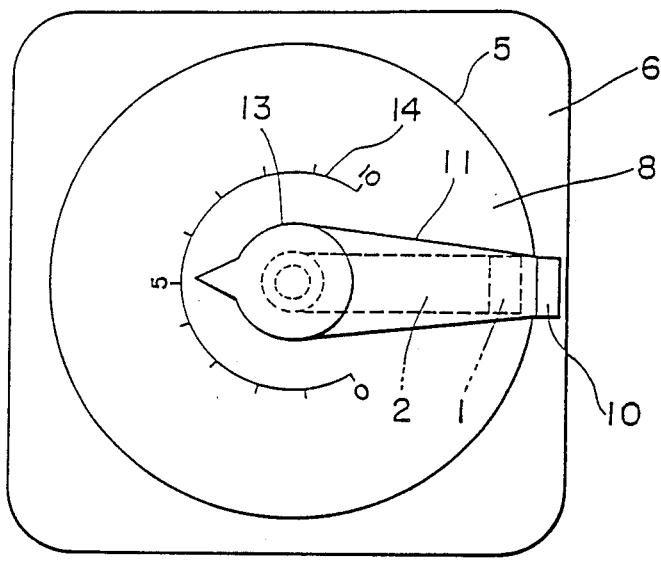
FIG. 1 is a plan view of an embodiment according to the invention.

In the drawings, symbol T designates transistor; R, resistor; C, capacitor; D, diode; H, transformer; and S, power switch.

Figure 2:
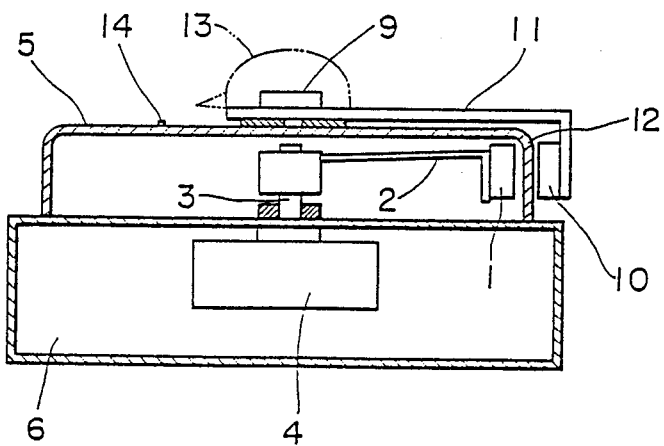
FIG. 2 is the vertical sectional view of the embodiment.

FIGS. 1 and 2 illustrate a variable resistor usable in the invention. In this variable resistor, arm member (2) having magnet (1) at its end is fixed about shaft (3) of rotary variable resistor (4) comprising a resistive element and a sliding member that moves in contact with the resistive element when shaft (3) rotates. Arm member (2) and rotary variable resistor (4) are enclosed in moistureproof container (6) having cylindrical projection (5). Stopper (9) is used to rotatably attach L-shaped guide member (11) having magnet (10) to flat surface (8) of projection (5) so that one pole of magnet (10) can face to the opposite pole of magnet (1) across cylindrical wall (12) of projection (5). Knob (13) is attached to stopper (9), while dial (14) is provided on flat surface (8) of projection (5).

By dialing knob (13) according to dial (14) to move guide member (11), arm member (2) and shaft (3) are rotated magnetically in association with the movement of guide member (11). Thus, a desired level of electric resistance can be attained with variable resistance (4). A desired level of low-frequency voltage can be obtained from a low-frequency oscillator by inserting the variable resistor between the output terminal of the low-frequency oscillator and an electrode, and dialing knob (13) according to dial (14).

Figure 3:
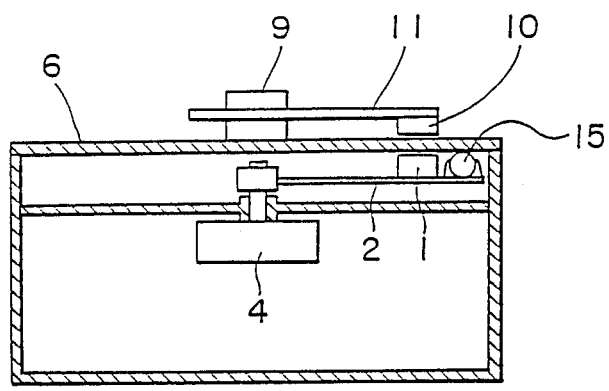
FIG. 3 is the vertical sectional view of another embodiment according to the invention.

FIG. 3 shows another embodiment according to the invention, wherein moistureproof container (6) is shaped into a cylinder by providing in the embodiment in FIG. 1 bearing (15), such as a ball or roller bearing, between arm member (2) and the inside wall of moistureproof container (6).

This embodiment is characterized in that it can be produced in a smaller size and at a lower cost in comparison with the previous embodiment.

Variable resistor (4) enclosed in moistureproof container (6) may be a slide variable resistor, and should not be restricted to a rotary variable resistor as shown in FIGS. 1 and 3. In case a slide variable resistor is used, a linear resistive element and a sliding member with magnet are enclosed in moistureproof container (6) in such manner that the sliding member moves in contact with the resistive element, while a guide member having a magnet is movably attached outside container (6) at an appropriate distance from the sliding member along with the resistive element.

Although either magnet (1) or (10) in FIG. 1 and 3 may be a magnetic piece such as that of iron or nickel, an increased attraction and a -stable operation can be attained by making them both with magnets.

The arm member and/or guide member consists partially or entirely of magnets or a magnetic piece.

Figure 4:
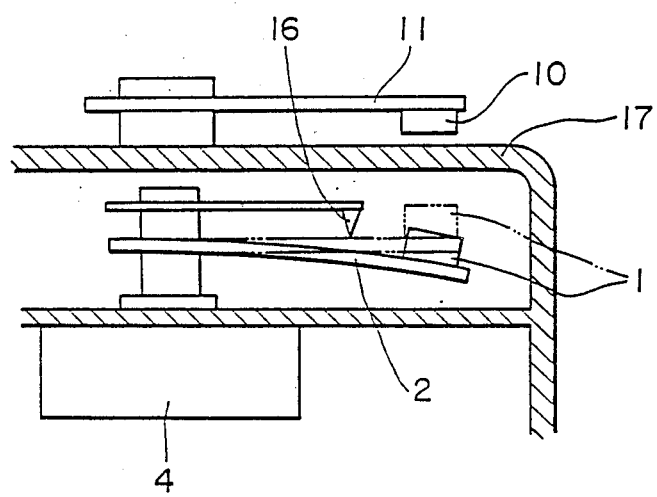
FIGS. 4 and 5 are switch mechanisms of the variable resistors usable in the invention.
Figure 5:
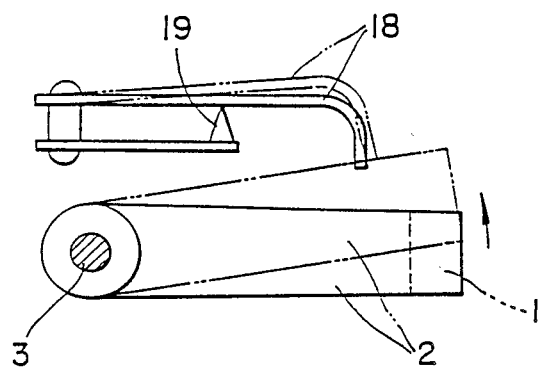

FIGS. 4 and 5 illustrate a switch structure that can be advantageously used in the device according to the invention.

In the example as shown in FIG. 4, spring arm member (2) and contact (16) are attached around shaft (3) of rotary variable resistor (4) in such manner that they move together and attract each other into conduction when one pole of magnet (1) faces opposite the pole of magnet (10) across side wall (17) of moistureproof container (6).

FIG. 5 is illustrative of a power switch wherein arm member (2) contacts with contact (18) to separate contacts (18) and (19) when it is at the minimum resistance position.

Figure 6:
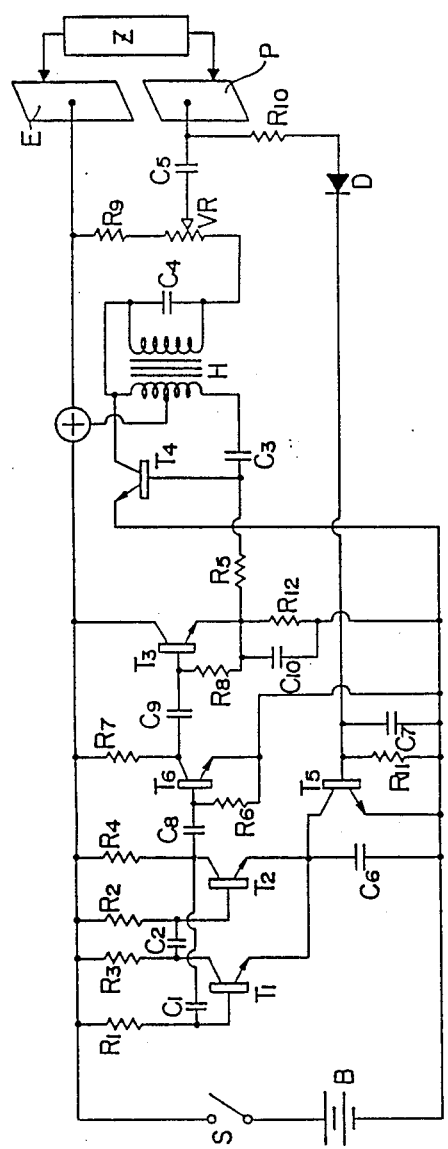
FIG. 6 is the circuit of a low-frequency oscillator usable in the invention.

FIG. 6 is the circuit of a low-frequency oscillator usable in the invention.

Figure 7:
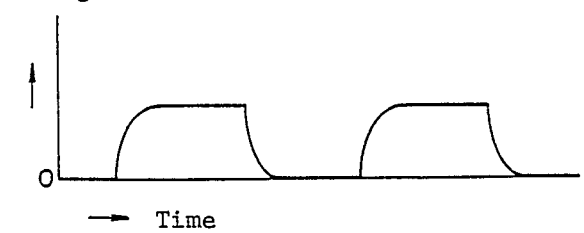
FIGS. 7 and 8 are the output waveform in the low-frequency oscillator.
Figure 8:
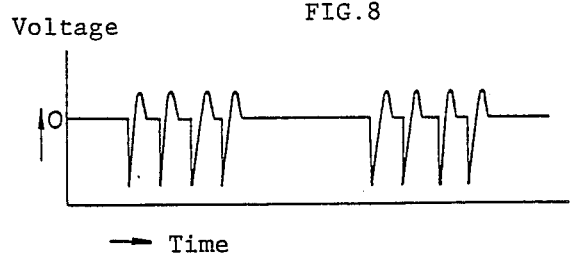

In this circuit, the multivibrator comprising transistors $T_1$ and $T_2$ oscillates a positive square wave, for example, having a pulse interval of 0.1–10 seconds and a pulse width of 0.1–10 seconds, which is then modified by transistor $T_3$ and resistor $R_5$ into a saturated wave voltage as shown in FIG. 7. The blocking oscillator including transistor $T_4$ is to generate a diphasic action potential, and the transistor becomes conductive whenever the saturated wave voltage supplied to the base comes to the positive region. Thus, as shown in FIG. 8, the blocking oscillator generates a diphasic action potential at time intervals equal to the pulse width of the square wave. When dispersive electrode E is placed, for example, on a non-affected site of the skin or in bath water and active electrode P comes nearly to or on load Z such as subject's body, the area between dispersive and active electrodes E and P becomes conductive through load Z. When this occurs, the current from dispersive electrode E charges capacitor $C_{10}$ through active electrode P, resistor $R_{10}$, diode D, and resistor $R_{11}$, and the voltage across capacitor $C_7$ conducts transistor $T_5$, and transistors $T_I$ and $T_2$ receive the emitter current and the multivibrator begins oscillation. The output square wave voltage is modified by transistor $T_6$ into a saturated wave voltage, and supplied to the base of transistor $T_4$ through resistor $R_5$ and the emitter follower circuit including transistor $T_3$. Transistor $T_4$ generates diphasic action potential when the voltage supplied to the base is not zero, and the output is controlled with variable resistor VR and then supplied between active and dispersive electrodes P and E.

Discharge of battery B never continues if the subject forgets to open power switch S because conduction of transistor $T_5$ is interrupted and operation of the multivibrator and blocking oscillator is stopped when no current flows across dispersive and active electrodes E and P.

Since in the device according to the invention the variable resistor is not exposed to moisture even when used in a humid environment such as a bath, the moisture never disturbs the operation of the device.

Since the variable resistor can be immersed in bath water, the subject can control while in the bath the dosage of low-frequency voltage. Thus, the device can be advantageously used in the improvement and treatment of blood circulation, muscular strength, muscular fatigue, massage, and hemorrhoids.

More particularly, the device equipped with an oscillator circuit, frequency of about 10–300 hertz, exerts a remarkable therapeutic effect when used while taking a bath: At a frequency of 100 hertz or lower, preferably, 10–70 hertz, the device is effective in improvement and treatment of blood circulation, muscular strength, fatigue and hemorrhoids; and at a frequency of 100–300 hertz, in prevention of alopecia as well as in acceleration and regeneration of hair.

Having described specific embodiments of my invention, it is believed obvious that modifications and variations of my invention are possible in the light of the above teachings.

I claim:

1. A device to effect low-frequency electrotherapy in a humid environment, comprising:
    an electrode that acts as a dispersive electrode when in use;
    another electrode that acts as an active electrode when in use;
    a transistorized multivibrator generating a positive square wave with a pulse interval of 0.1–10 seconds and a pulse width of 0.1–10 seconds when a load is connected between the electrodes;
    a transistorized blocking oscillator generating a diphasic action potential with a frequency of 10–300 hertz, said diphasic action potential having a spike in respective voltage components in positive and negative directions and said blocking oscillator having an output terminal connected with said active electrode;
    a transistorized saturating circuit having an input terminal connected with an output terminal of said multivibrator, and also having an output terminal connected with a base of said transistorized blocking oscillator;
    a battery means to energize the whole circuit; and
    a variable resistor connected between the output terminal of said blocking oscillator and said active electrode, said variable resistor comprising;
    a resistive element;
    a sliding member slidable along with said resistive element;
    a moisture proof container enclosing said resistive element and sliding member; and
    a guide member attached outside said container, said guide member is movable magnetically in association with said sliding member.

2. The device of claim 1 wherein said variable resistor has a switch connection on said variable resistor.

3. The device of claim 1 wherein said variable resistor is rotary variable resistor.

4. The device of claim 1 wherein said variable resistor is a slide variable resistor.

5. The device of claim 1 wherein at least one of said sliding member and said guide member is at least partially a magnet.

6. The device of claim 5 wherein both said sliding member and said guide member are at least partially a magnet.

7. The device of claim 1 wherein said variable resistor is immersed in bath water during use.

* * * * *